US012642494B2

(12) United States Patent
Hirano et al.

(10) Patent No.: US 12,642,494 B2
(45) Date of Patent: Jun. 2, 2026

(54) X-RAY COMPUTED TOMOGRAPHY APPARATUS, INFORMATION PROCESSING SYSTEM, INFORMATION PROCESSING METHOD, AND NON-TRANSITORY COMPUTER-READABLE MEDIUM

(71) Applicant: CANON KABUSHIKI KAISHA, Tokyo (JP)

(72) Inventors: Yoshinori Hirano, Chiba (JP); Ryuta Ueda, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 284 days.

(21) Appl. No.: 18/500,561

(22) Filed: Nov. 2, 2023

(65) Prior Publication Data
US 2024/0148344 A1 May 9, 2024

(30) Foreign Application Priority Data
Nov. 7, 2022 (JP) ................................. 2022-177876

(51) Int. Cl.
| | |
|---|---|
| *A61B 6/03* | (2006.01) |
| *A61B 6/00* | (2024.01) |
| *G06T 5/50* | (2006.01) |
| *G06T 7/00* | (2017.01) |

(52) U.S. Cl.
CPC ............ *A61B 6/032* (2013.01); *A61B 6/5235* (2013.01); *G06T 5/50* (2013.01); *G06T 7/0012* (2013.01); *G06T 2207/10081* (2013.01); *G06T 2207/20221* (2013.01); *G06T 2207/30096* (2013.01)

(58) Field of Classification Search
None
See application file for complete search history.

(56) References Cited

U.S. PATENT DOCUMENTS

| | | | | | |
|---|---|---|---|---|---|
| 2020/0321118 | A1* | 10/2020 | Kim | .......................... | G06N 3/09 |
| 2020/0335202 | A1* | 10/2020 | Kawagishi | ............. | G06V 10/25 |
| 2020/0388395 | A1* | 12/2020 | Umezawa | ................ | G06N 7/01 |

(Continued)

FOREIGN PATENT DOCUMENTS

| | | |
|---|---|---|
| CN | 103519838 A | 1/2014 |
| CN | 105188545 A | 12/2015 |

(Continued)

*Primary Examiner* — Nancy Bitar
(74) *Attorney, Agent, or Firm* — Canon U.S.A., Inc. IP Division

(57) ABSTRACT

An X-ray computed tomography (CT) apparatus includes an X-ray tube configured to radiate X-rays; a detector configured to detect X-rays radiated by the X-ray tube and passed through a subject; a reconstruction processing unit configured to reconstruct imaging data output by the detector and generate CT image data and material decomposition image data; a first inference unit configured to perform inference on the material decomposition image data; a second inference unit configured to perform inference on the CT image data; a third inference unit configured to perform inference on composite image data; a selection unit configured to, in a case where an inference result of the first inference unit is different from an inference result of the second inference unit, select an inference result of the third inference unit; and a display control unit configured to cause the selected inference result to be displayed.

14 Claims, 7 Drawing Sheets

(56)          References Cited

U.S. PATENT DOCUMENTS

2021/0282732 A1 *   9/2021   Qi ......................... A61B 6/5282
2022/0101048 A1 *   3/2022   Tan ........................ A61B 5/055
2024/0104797 A1 *   3/2024   Gong ................... G06T 11/008

FOREIGN PATENT DOCUMENTS

CN          107133995  A      9/2017
CN          212415753  U      1/2021
CN          112446855  A      3/2021
CN          114565695  A      5/2022
CN          114867416  A      8/2022
CN          115105107  A      9/2022
JP          2018175866 A      11/2018

* cited by examiner

X-RAY COMPUTED TOMOGRAPHY APPARATUS, INFORMATION PROCESSING SYSTEM, INFORMATION PROCESSING METHOD, AND NON-TRANSITORY COMPUTER-READABLE MEDIUM

BACKGROUND OF THE DISCLOSURE

Field of the Disclosure

The present disclosure relates to an X-ray computed tomography (CT) apparatus equipped with a photon counting CT function, an information processing system, an information processing method, and a non-transitory computer-readable medium.

Description of the Related Art

An X-ray computed tomography (CT) apparatus equipped with a photon counting CT function counts individual incident X-rays and measures the energy of the incident X-rays, thereby obtaining an X-ray spectrum. With use of the obtained X-ray spectrum, the X-ray CT apparatus is capable of identifying a material included in a subject and generating material decomposition image data. The X-ray CT apparatus equipped with a photon counting CT function is also capable of reconstructing CT image data (integral image data) (for example, Japanese Patent Laid-Open No. 2018-175866).

On the other hand, inference tasks performed by a neural network include a classification task of classifying a class of image data and a detection task of detecting what is captured at which position in image data.

An inference result may vary depending on whether an inference task is performed on material decomposition image data or CT image data (integral image data) obtained by an X-ray CT apparatus equipped with a photon counting CT function.

SUMMARY OF THE DISCLOSURE

The present disclosure is directed to displaying an appropriate inference result.

An X-ray CT apparatus according to an embodiment of the present disclosure includes an X-ray tube configured to radiate X-rays; a detector configured to detect X-rays radiated by the X-ray tube and passed through a subject; a reconstruction processing unit configured to reconstruct imaging data output by the detector and generate CT image data and material decomposition image data; a first inference unit configured to perform inference on the material decomposition image data; a second inference unit configured to perform inference on the CT image data; a third inference unit configured to perform inference on composite image data composed of the CT image data and the material decomposition image data; a selection unit configured to, in a case where an inference result of the first inference unit is different from an inference result of the second inference unit, select an inference result of the third inference unit; and a display control unit configured to cause the selected inference result of the third inference unit to be displayed.

An information processing system according to an embodiment of the present disclosure includes a first inference unit configured to perform inference on material decomposition image data generated by reconstructing imaging data output by a detector; a second inference unit configured to perform inference on image data generated by reconstructing the imaging data output by the detector; a third inference unit configured to perform inference on composite image data composed of the image data and the material decomposition image data; a selection unit configured to, in a case where an inference result of the first inference unit is different from an inference result of the second inference unit, select an inference result of the third inference unit; and a display control unit configured to cause the selected inference result of the third inference unit to be displayed.

An information processing method according to an embodiment of the present disclosure includes performing inference on material decomposition image data generated by reconstructing imaging data output by a detector; performing inference on image data generated by reconstructing the imaging data output by the detector; selecting an inference result obtained by performing inference on composite image data composed of the image data and the material decomposition image data, in a case where an inference result obtained in the performing of the inference on the material decomposition image data is different from an inference result obtained in the performing of the inference on the image data; and causing the selected inference result to be displayed.

An X-ray CT apparatus according to an embodiment of the present disclosure includes an X-ray tube configured to radiate X-rays; a detector configured to detect X-rays radiated by the X-ray tube and passed through a subject; a reconstruction processing unit configured to reconstruct imaging data output by the detector and generate CT image data and material decomposition image data; a first inference unit configured to perform inference on the material decomposition image data; a second inference unit configured to perform inference on the CT image data; a third inference unit configured to perform inference on composite image data composed of the CT image data and the material decomposition image data; an image analysis unit configured to analyze the material decomposition image data and obtain content information of a predetermined material included in the material decomposition image data or content information of a predetermined lesion included in the material decomposition image data; a selection unit configured to, based on the content information of the predetermined material included in the material decomposition image data or the content information of the predetermined lesion included in the material decomposition image data, select at least one of an inference result of the first inference unit, an inference result of the second inference unit, and an inference result of the third inference unit; and a display control unit configured to cause the selected inference result to be displayed.

An information processing system according to an embodiment of the present disclosure includes a first inference unit configured to perform inference on material decomposition image data generated by reconstructing imaging data output by a detector; a second inference unit configured to perform inference on image data generated by reconstructing the imaging data output by the detector; a third inference unit configured to perform inference on composite image data composed of the image data and the material decomposition image data; an image analysis unit configured to analyze the material decomposition image data and obtain content information of a predetermined material included in the material decomposition image data or content information of a predetermined lesion included in the material decomposition image data; a selection unit configured to, based on the content information of the predetermined material included in the material decomposition image data or the content information of the predetermined lesion included in the material decomposition image data, select at least one of an inference result of the first inference unit, an inference result of the second inference unit, and an inference result of the third inference unit; and a display control unit configured to cause the selected inference result to be displayed.

An information processing method according to an embodiment of the present disclosure includes analyzing material decomposition image data generated by reconstructing imaging data output by a detector and obtaining content information of a predetermined material included in the material decomposition image data or content information of a predetermined lesion included in the material decomposition image data; and performing, based on the content information of the predetermined material included in the material decomposition image data or the content information of the predetermined lesion included in the material decomposition image data, inference on at least one of the material decomposition image data, image data, and composite image data composed of the material decomposition image data and the image data, and causing an inference result to be displayed.

An X-ray CT apparatus according to an embodiment of the present disclosure includes an X-ray tube configured to radiate X-rays; a detector configured to detect X-rays radiated by the X-ray tube and passed through a subject; a reconstruction processing unit configured to reconstruct imaging data output by the detector and generate CT image data and material decomposition image data; a first inference unit configured to perform inference on the material decomposition image data; a second inference unit configured to perform inference on the CT image data; a third inference unit configured to perform inference on composite image data composed of the CT image data and the material decomposition image data; and a selection unit configured to select at least one of an inference result of the first inference unit, an inference result of the second inference unit, and an inference result of the third inference unit in accordance with an examination order.

An information processing system according to an embodiment of the present disclosure includes a first inference unit configured to perform inference on material decomposition image data generated by reconstructing imaging data output by a detector; a second inference unit configured to perform inference on image data generated by reconstructing the imaging data output by the detector; a third inference unit configured to perform inference on composite image data composed of the image data and the material decomposition image data; a selection unit configured to select at least one of an inference result of the first inference unit, an inference result of the second inference unit, and an inference result of the third inference unit in accordance with an examination order; and a display control unit configured to cause the selected inference result to be displayed.

An information processing method according to an embodiment of the present disclosure includes generating image data and material decomposition image data that are based on X-rays radiated by an X-ray tube and passed through a subject, and composite image data composed of the image data and the material decomposition image data; and performing inference on at least one of the material decomposition image data, the image data, and the composite image data composed of the image data and the material decomposition image data in accordance with an examination order, and causing an inference result to be displayed.

Further features of the present disclosure will become apparent from the following description of exemplary embodiments with reference to the attached drawings.

DESCRIPTION OF THE EMBODIMENTS

Figure 1:
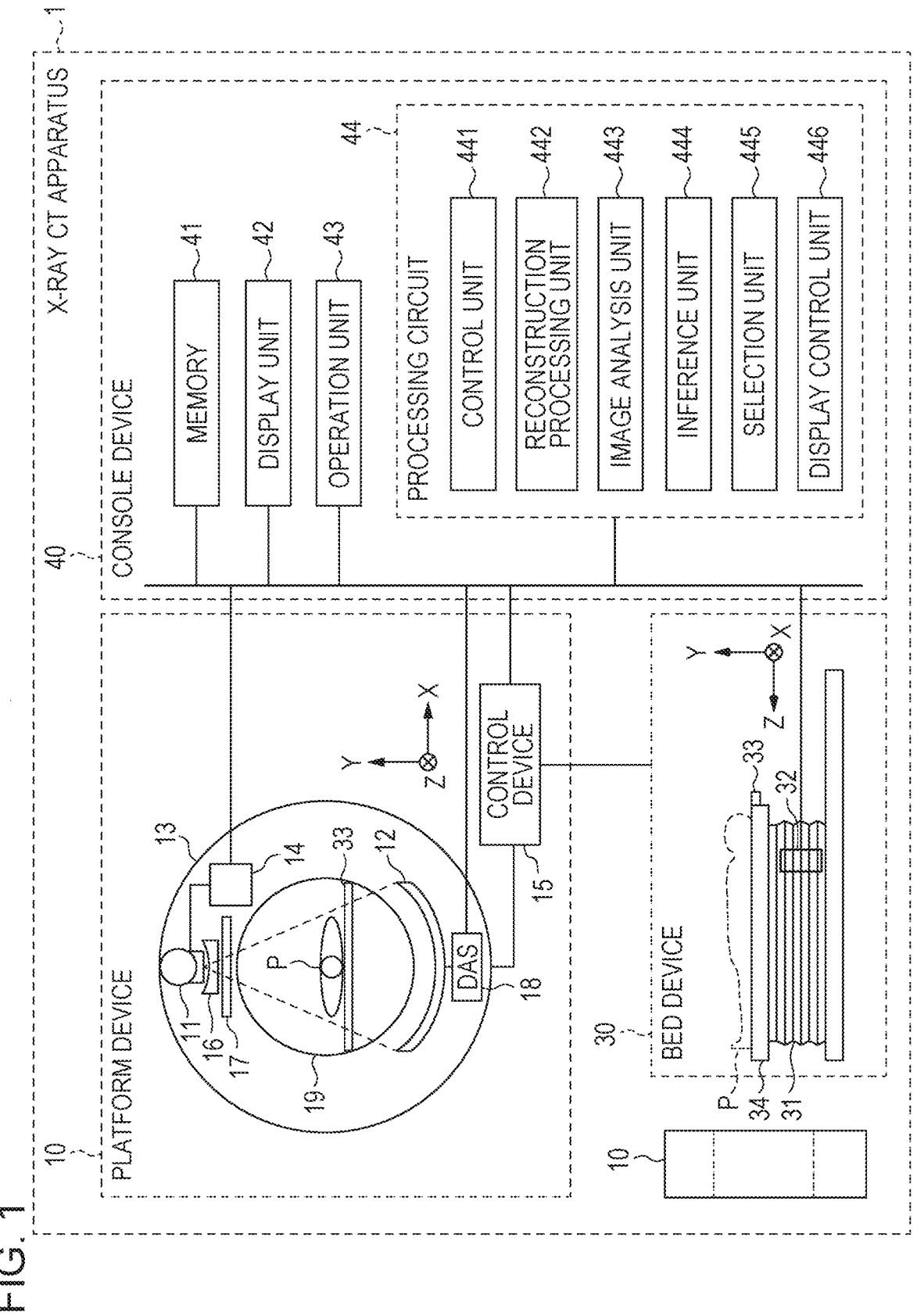
FIG. 1 is a diagram illustrating an example configuration of an X-ray computed tomography (CT) apparatus according to an embodiment of the present disclosure.

Hereinafter, an X-ray computed tomography (CT) apparatus, an information processing system, an information processing method, and a non-transitory computer-readable medium storing a program according to embodiments will be described with reference to the drawings. The parts denoted by the same reference numerals perform similar operations, and repeated description will be omitted as appropriate. Hereinafter, embodiments will be described with reference to the drawings.

A first embodiment of the present disclosure will be described with reference to FIGS. 1 to 5. An example configuration of an X-ray CT apparatus according to the first embodiment will be described with reference to FIG. 1. An X-ray CT apparatus 1 illustrated in FIG. 1 includes a platform device (gantry) 10, a bed device 30, and a console device 40. In the embodiments, a rotational axis direction of a rotary frame 13 or a longitudinal direction of a top plate 33 of the bed device 30 in a non-tilted state is defined as a Z-axis direction, an axis direction orthogonal to the Z-axis direction and horizontal to a floor surface is defined as an X-axis direction, and an axis direction orthogonal to the Z-axis direction and vertical to the floor surface is defined as a Y-axis direction.

For example, the platform device 10 and the bed device 30 are installed in a CT examination room, and the console device 40 is installed in a control room adjacent to the CT examination room. The console device 40 need not necessarily be installed in the control room. For example, the console device 40 may be installed in the room having the platform device 10 and the bed device 30 installed therein. In any case, the platform device 10, the bed device 30, and the console device 40 are connected to each other in a wired or wireless manner so as to be capable of communicating with each other.

The platform device 10 is a scanning device having a configuration for performing X-ray CT imaging on a subject P. The platform device 10 includes an X-ray tube 11, a detector 12, the rotary frame 13, an X-ray high voltage device 14, a control device 15, a wedge 16, a collimator 17, and a data collection device 18 (hereinafter also referred to as a data acquisition system (DAS)).

Here, only a part of the configuration is illustrated for convenience of description.

The X-ray tube 11 is a vacuum tube that generates X-rays by radiating thermoelectrons from a cathode (filament) toward an anode (target) by application of a high voltage and supply of a filament current from the X-ray high voltage device 14. Specifically, X-rays are generated as a result of thermoelectrons colliding with the target. For example, the X-ray tube 11 may be a rotating anode X-ray tube that generates X-rays by radiating thermoelectrons to a rotating anode. The X-rays generated by the X-ray tube 11 are shaped into a cone beam shape via, for example, the collimator 17, and are radiated to the subject P. The X-ray tube 11 is an example of an X-ray generation unit.

The detector 12 detects X-rays radiated by the X-ray tube 11 and passed through the subject P, and outputs a signal corresponding to an X-ray dosage to the DAS 18. The detector 12 includes, for example, a plurality of X-ray detection element rows in each of which a plurality of X-ray detection elements are arranged in a channel direction along one arc with the focal point of the X-ray tube 11 being the center. The detector 12 has, for example, a row structure in which a plurality of X-ray detection element rows, in each of which a plurality of X-ray detection elements are arranged in the channel direction, are arranged in a slice direction (row direction). The detector 12 is a photon-counting detector. A reconstruction processing unit is capable of reconstructing CT image data (integral image data) with a high S/N ratio by counting the number of photons of X-rays passed through the subject P by using the photon-counting detector.

The detector 12 may be classified into an energy integration function or a photon counting function depending on the method for measurement performed on a converted signal by the DAS 18. The energy integration function integrates the energy of X-rays passed through the subject P for a certain period of time, thereby measuring the total sum of the energy of the X-rays passed during the certain period of time. The photon counting function measures the number of X-ray photons included in X-rays passed through the subject P, for each of a plurality of energy bands (also referred to as energy bins or simply as bins). This makes it possible to perform material decomposition based on imaging data obtained for each energy band. Here, an imaging mode in which material decomposition is performed is referred to as a material decomposition mode (material decomposition image mode), and an imaging mode in which material decomposition is not performed is referred to as a non-material-decomposition mode (integral image mode).

The rotary frame 13 supports an X-ray generation unit and an X-ray detection unit so as to be rotatable around the rotational axis Z. Specifically, the rotary frame 13 is an annular frame that supports the X-ray tube 11 and the detector 12 so as to be opposed to each other, and rotates the X-ray tube 11 and the detector 12 by the control device 15. The rotary frame 13 is rotatably supported by a fixed frame (not illustrated) formed of a metal such as aluminum. Specifically, the rotary frame 13 is connected to an edge portion of the fixed frame via a bearing. The rotary frame 13 receives power from a driving mechanism of the control device 15 and rotates around the rotational axis Z at a constant angular velocity.

The rotary frame 13 further includes and supports the X-ray high voltage device 14 and the DAS 18 in addition to the X-ray tube 11 and the detector 12. The rotary frame 13 is accommodated in a substantially cylindrical housing having an opening (bore) 19 serving as an imaging space. The opening 19 substantially coincides with the FOV. The center axis of the opening 19 coincides with the rotational axis Z of the rotary frame 13. Imaging data generated by the DAS 18 is transmitted, for example, from a transmitter including a light emitting diode (LED) to a receiver (not illustrated) including a photodiode provided in a non-rotating portion (fixed frame) of the platform device 10 by optical communication, and is transferred to the console device 40. The method of transmitting the imaging data from the rotary frame 13 to the non-rotating portion of the platform device 10 is not limited to optical communication, and any non-contact data transmission method may be employed.

The X-ray high voltage device 14 includes electric circuits such as a transformer and a rectifier, a high voltage generator having a function of generating a high voltage to be applied to the X-ray tube 11 and a filament current to be supplied to the X-ray tube 11, and an X-ray controller that controls an output voltage in accordance with X-rays radiated by the X-ray tube 11. The high voltage generator may employ a transformer scheme or an inverter scheme. The X-ray high voltage device 14 may be provided in the rotary frame 13 or on the fixed frame side of the platform device 10.

The control device 15 includes a processing circuit including a central processing unit (CPU) or the like, and a driving mechanism such as a motor or an actuator. The processing circuit includes, as hardware resources, a processor such as a CPU or a micro processing unit (MPU), and a memory such as a read only memory (ROM) or a random access memory (RAM). The control device 15 may be implemented by an application specific integrated circuit (ASIC), a field programmable gate array (FPGA), another complex programmable logic device (CPLD), or a simple programmable logic device (SPLD). The control device 15 controls the X-ray high voltage device 14, the DAS 18, and so forth in accordance with instructions from the console device 40. The processor implements the above control by reading and executing a program stored in the memory.

The wedge 16 is a filter for adjusting the dosage of X-rays radiated by the X-ray tube 11.

Specifically, the wedge 16 is a filter that passes and attenuates the X-rays radiated by the X-ray tube 11 so that the X-rays radiated from the X-ray tube 11 to the subject P have a predetermined distribution. For example, the wedge 16 (a wedge filter or a bow-tie filter) is a filter obtained by processing aluminum to have a predetermined target angle and a predetermined thickness.

The collimator 17 is a lead plate or the like for narrowing down the radiation range of the X-rays passed through the wedge 16, and has a slit in accordance with a combination of a plurality of lead plates or the like. The collimator 17 may be referred to as an X-ray aperture.

The DAS 18 generates, for each of a plurality of energy bands, digital data (also referred to as imaging data) indicating a count value of X-ray photons detected by the detector 12. The imaging data is a data set of count values identified by the channel number, row number, view number indicating an acquisition view (projection angle), and energy bin number of the X-ray detection elements as a generation source. The DAS 18 is implemented by, for example, an application specific integrated circuit (ASIC) having a circuit element capable of generating imaging data. The imaging data is transferred to the console device 40.

The bed device 30 is a device on which the subject P to be scanned is to be placed and moved, and includes a base 31, a bed driving device 32, the top plate 33, and a support frame 34. The base 31 is a housing that supports the support frame 34 so as to be movable in the vertical direction.

The bed driving device 32 is a motor or an actuator that moves the top plate 33 on which the subject P is placed in the longitudinal direction of the top plate 33. The bed driving device 32 moves the top plate 33 in accordance with control by the console device 40 or the control device 15. For example, the bed driving device 32 moves the top plate 33 in a direction orthogonal to the subject P so that the body axis of the subject P placed on the top plate 33 coincides with the central axis of the opening of the rotary frame 13. The bed driving device 32 may move the top plate 33 in the direction of the body axis of the subject P in accordance with X-ray CT imaging performed using the platform device 10. The bed driving device 32 generates power by being driven at a rotation speed corresponding to the duty ratio or the like of a driving signal from the control device 15. The bed driving device 32 is implemented by, for example, a motor such as a direct drive motor or a servo motor.

The top plate 33 provided on the upper surface of the support frame 34 is a plate on which the subject P is to be placed. The bed driving device 32 may move, in addition to the top plate 33, the support frame 34 in the longitudinal direction of the top plate 33.

The console device 40 includes a memory 41, a display unit 42, an operation unit 43, and a processing circuit 44. Data communication among the memory 41, the display unit 42, the operation unit 43, and the processing circuit 44 is performed via a bus. Although the console device 40 is described as a separate body separated from the platform device 10, the console device 40 or some of the constituent elements of the console device 40 may be included in the platform device 10.

The memory 41 is a storage device such as a hard disk drive (HDD), a solid state drive (SSD), or an integrated circuit storage device that stores various kinds of information.

The memory 41 stores, for example, imaging data and reconstructed image data. The memory 41 is not limited to an HDD or SSD, and may be a drive device that reads and writes various kinds of information from and to a portable storage medium such as a compact disc (CD), a digital versatile disc (DVD), or a flash memory, a semiconductor memory element such as a random access memory (RAM), or the like. The storage area of the memory 41 may be in the X-ray CT apparatus 1 or in an external storage device connected via a network. For example, the memory 41 stores data of a CT image and a display image. The memory 41 also stores a control program according to an embodiment.

The display unit 42 displays various kinds of information. For example, the display unit 42 outputs a medical image (CT image) generated by the processing circuit 44 and a graphical user interface (GUI) for receiving various operations from an operator. As the display unit 42, for example, a liquid crystal display (LCD) unit, a cathode ray tube (CRT) display unit, an organic electroluminescence display (OELD) unit, a plasma display unit, or any other display unit may be used as appropriate. The display unit 42 may be provided in the platform device 10. The display unit 42 may be of a desktop type or may be constituted by a tablet terminal or the like capable of wirelessly communicating with the main body of the console device 40.

The operation unit 43 receives various input operations from the operator, converts the received input operations into electric signals, and outputs the electric signals to the processing circuit 44. For example, the operation unit 43 receives, from the operator, an acquisition condition for acquiring imaging data, a reconstruction condition for reconstructing a CT image, an image processing condition for generating a post-processed image from a CT image, and the like. As the operation unit 43, for example, a mouse, a keyboard, a trackball, a switch, a button, a joystick, a touch pad, or a touch panel display unit may be used as appropriate. In the embodiment, the operation unit 43 is not limited to a unit including a physical operation component such as a mouse, a keyboard, a trackball, a switch, a button, a joystick, a touch pad, or a touch panel display unit. For example, an electric signal processing circuit that receives an electric signal corresponding to an input operation from an external input device provided separately from the apparatus and outputs the electric signal to the processing circuit 44 is also included in examples of the operation unit 43. The operation unit 43 may be provided in the platform device 10. The operation unit 43 may be constituted by a tablet terminal or the like capable of wirelessly communicating with the main body of the console device 40.

The processing circuit 44 controls the operation of the entire X-ray CT apparatus 1 in accordance with an electric signal of an input operation output from the operation unit 43. For example, the processing circuit 44 includes, as hardware resources, a processor such as a CPU, an MPU, or a graphics processing unit (GPU), and a memory such as a ROM or a RAM. The processing circuit 44 implements, by the processor that executes a program loaded in the memory, a control unit 441, a reconstruction processing unit 442, an image analysis unit 443, an inference unit 444, a selection unit 445, and a display control unit 446. The individual functions (the control unit 441, the reconstruction processing unit 442, the image analysis unit 443, the inference unit 444, the selection unit 445, and the display control unit 446) are not necessarily implemented by a single processing circuit. A plurality of independent processors may be combined to constitute a processing circuit, and the individual processors may execute a program to implement the individual functions.

The control unit 441 controls each function of the processing circuit 44 in accordance with an input operation received from the operator via the operation unit 43. Specifically, the control unit 441 reads out a control program stored in the memory 41, loads the control program into the memory in the processing circuit 44, and controls each unit of the X-ray CT apparatus 1 in accordance with the loaded control program. The control unit 441 performs preprocessing, such as logarithmic transformation processing, offset correction processing, inter-channel sensitivity correction processing, or beam hardening correction, on the imaging data output from the DAS 18, thereby generating preprocessed imaging data.

The reconstruction processing unit 442 has a function of generating CT image data, based on the imaging data output by the detector 12 (DAS 18). The reconstruction processing unit 442 reconstructs CT image data by performing, for example, back projection processing on the imaging data stored in the memory 41. The back projection processing may be, for example, back projection processing based on a filtered back projection (FBP) method. The reconstruction processing unit 442 may perform reconstruction processing by using, for example, successive approximations. The reconstruction processing unit 442 generates CT image data by performing various kinds of image processing on the CT image data. The reconstruction processing unit 442 stores the reconstructed CT image data and the CT image data generated through various kinds of image processing in the memory 41.

The reconstruction processing unit 442 calculates energy integration data by using the sum (total value) of the counts of individual energy bins or the sum of the products of the representative values and the counts of energy bins, which is a signal obtained by the photon-counting detector 12. The reconstruction processing unit 442 is capable of reconstructing CT image data (integral image data) by using the energy integration data.

As an application of the photon-counting X-ray CT apparatus 1, there is a technique of determining the type, the amount, the density, and so forth of a material included in the subject P by using the fact that each material has different X-ray absorption characteristic. This is called material decomposition. For example, the reconstruction processing unit 442 is capable of performing material decomposition on imaging data and acquiring material decomposition information. The reconstruction processing unit 442 is also capable of reconstructing material decomposition image data indicating material decomposition by using material decomposition information, which is a result of material decomposition.

For example, imaging data generated from a counting result obtained by the photon-counting X-ray CT apparatus 1 includes information on the energy spectrum of X-rays attenuated as a result of passing through the subject P. Thus, the reconstruction processing unit 442 is capable of reconstructing, for example, material decomposition image data obtained by imaging a specific energy component.

The image analysis unit 443 analyzes material decomposition image data. By analyzing the material decomposition image data, the image analysis unit 443 is capable of obtaining how much of a predetermined material is included in the material decomposition image data, or how much of a predetermined lesion is included in the material decomposition image data.

The inference unit 444 is capable of performing inference on material decomposition image data. The inference unit 444 is capable of performing inference on CT image data (integral image data). The inference unit 444 is capable of performing inference on composite image data composed of material decomposition image data and CT image data (integral image data). Thus, the inference unit 444 is capable of performing inference on each of material decomposition image data, CT image data, and composite image data composed of material decomposition image data and CT image data.

Figure 2:
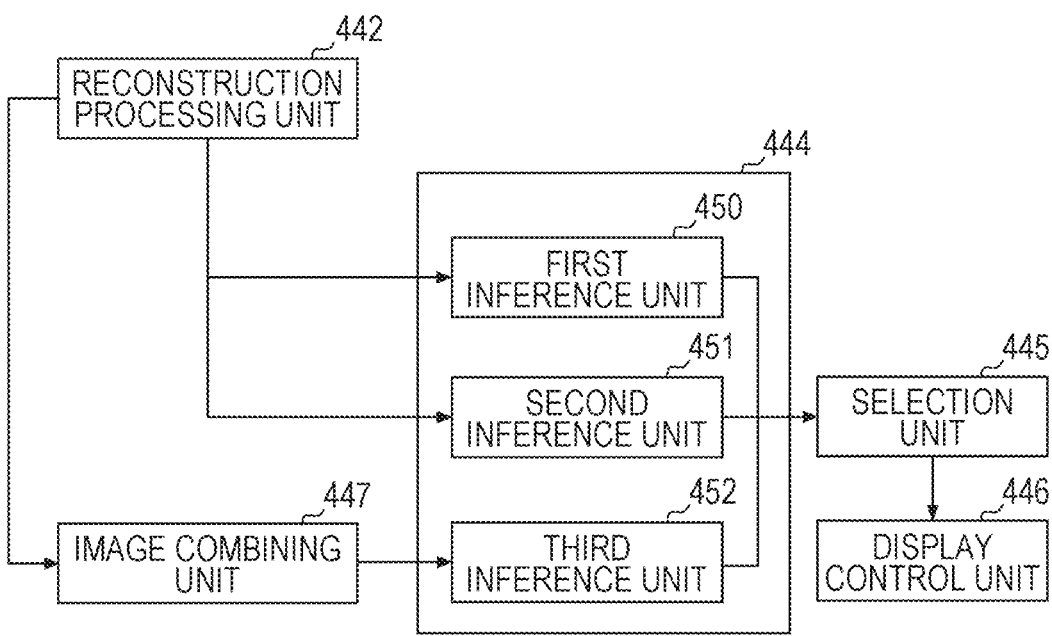
FIG. 2 is a diagram illustrating an example of a peripheral configuration of an inference unit of an X-ray CT apparatus according to an embodiment of the present disclosure.

Specifically, as illustrated in FIG. 2, the inference unit 444 includes a first inference unit 450, a second inference unit 451, and a third inference unit 452. The first inference unit 450 performs inference on material decomposition image data by using a neural network. The second inference unit 451 performs inference on CT image data by using a neural network. The third inference unit 452 performs inference on composite image data composed of material decomposition image data and CT image data by using a neural network.

The first inference unit 450 obtains teaching data in advance. The teaching data is determined in accordance with an inference task performed by the neural network or a classification target.

Examples of an inference task performed by the neural network include a classification task of classifying the class of material decomposition image data, a detection task of detecting which material is present at which position in material decomposition image data, and a segmentation task of extracting a target region from material decomposition image data. The material decomposition image data used as teaching data is material decomposition image data different from CT image data (integral image data).

At the time of training a neural network that performs a classification task, the first inference unit 450 obtains teaching data including a pair of material decomposition image data and a correct answer label, which is a label indicating a target material that is present in the material decomposition image data.

On the other hand, at the time of training a neural network that performs a detection task, the first inference unit 450 obtains, for material decomposition image data, teaching data including a pair of a region of interest (ROI) indicating the position of a target material that is present in the material decomposition image data and a correct answer image having a correct answer label, which is a label indicating the target.

At the time of training a neural network that performs a segmentation task, the first inference unit 450 obtains, for material decomposition image data, teaching data including a pair of position information of pixels of a target material that is present in the material decomposition image data and a correct answer image having a correct answer label, which is a label indicating the target material.

Similarly, the second inference unit 451 obtains teaching data in advance. The teaching data is determined in accordance with an inference task performed by the neural network or a classification target.

Examples of an inference task performed by the neural network include a classification task of classifying the class of CT image data (integral image data), a detection task of detecting which is present at which position in CT image data, and a segmentation task of extracting a target region from CT image data.

At the time of training a neural network that performs a classification task, the second inference unit 451 obtains teaching data including a pair of CT image data and a correct answer label, which is a label indicating a target that is present in the CT image data.

On the other hand, at the time of training a neural network that performs a detection task, the second inference unit 451 obtains, for CT image data, teaching data including a pair of a region of interest (ROI) indicating the position of a target that is present in the CT image data and a correct answer image having a correct answer label, which is a label indicating the target.

At the time of training a neural network that performs a segmentation task, the second inference unit 451 obtains, for CT image data, teaching data including a pair of position information of pixels of a target that is present in the CT image data and a correct answer image having a correct answer label, which is a label indicating the target.

An image combining unit 447 is included in the processing circuit 44. The image combining unit 447 combines material decomposition image data and CT image data (integral image data). Specifically, the image combining unit 447 performs registration of the material decomposition image data and CT image data, based on characteristic portions of the material decomposition image data and the CT image data, and thereby combines the material decomposition image data and the CT image data. The registration of the material decomposition image data and the CT image data may be performed for each slice.

The third inference unit 452, which performs inference on composite image data composed of material decomposition image data and CT image data (integral image data), obtains teaching data in advance. The teaching data is determined in accordance with an inference task performed by the neural network or a classification target.

Examples of an inference task performed by the neural network include a classification task of classifying the class of composite image data composed of material decomposition image data and CT image data (integral image data), a detection task of detecting which is present at which position in composite image data, and a segmentation task of extracting a target region from composite image data.

At the time of training a neural network that performs a classification task, the third inference unit 452 obtains teaching data including a pair of composite image data composed of material decomposition image data and CT image data (integral image data) and a correct answer label, which is a label indicating a target that is present in the composite image data.

On the other hand, at the time of training a neural network that performs a detection task, the third inference unit 452 obtains, for composite image data composed of material decomposition image data and CT image data (integral image data), teaching data including a pair of a region of interest (ROI) indicating the position of a target that is present in the composite image data and a correct answer image having a correct answer label, which is a label indicating the target.

At the time of training a neural network that performs a segmentation task, the third inference unit 452 obtains, for composite image data composed of material decomposition image data and CT image data (integral image data), teaching data including a pair of position information of pixels of a target that is present in the composite image data and a correct answer image having a correct answer label, which is a label indicating the target.

The selection unit 445 selects at least one of an inference result of the first inference unit 450 that performs inference on material decomposition image data, an inference result of the second inference unit 451 that performs inference on CT image data (integral image data), and an inference result of the third inference unit 452 that performs inference on composite image data composed of material decomposition image data and CT image data (integral image data).

That is, the selection unit 445 is capable of selecting which of the inference result of the first inference unit 450 that performs inference on material decomposition image data, the inference result of the second inference unit 451 that performs inference on CT image data (integral image data), and the inference result of the third inference unit 452 that performs inference on composite image data composed of material decomposition image data and CT image data (integral image data) is to be displayed on the display unit 42.

The selection unit 445 is also capable of selecting at least one of the inference result of the first inference unit 450, the inference result of the second inference unit 451, and the inference result of the third inference unit 452 in accordance with an examination order. Specifically, in a case where the examination order includes an examination regarding mammary glands (calcification examination), the selection unit 445 selects the inference result of the third inference unit 452 that performs inference on composite image data including calcium information and CT image data (integral image data). Alternatively, the selection unit 445 may select the inference result of the first inference unit 450 that performs inference on material decomposition image data including calcium information.

In a case where the examination order includes an examination using a contrast medium (iodine examination), the selection unit 445 selects the inference result of the third inference unit 452 that performs inference on composite image data composed of material decomposition image data including iodine information and CT image data (integral image data). Alternatively, the selection unit 445 may select the inference result of the first inference unit 450 that performs inference on material decomposition image data including iodine information. Furthermore, in a case where the examination order includes an examination regarding the presence/absence of metal (stent) (metal examination), the selection unit 445 selects the inference result of the third inference unit 452 that performs inference on composite image data composed of material decomposition image data including metal (stent) information and CT image data (integral image data). Alternatively, the selection unit 445 may select the inference result of the first inference unit 450 that performs inference on material decomposition image data including metal (stent) information.

That is, in a case where the examination order includes a predetermined first examination (calcification examination, iodine examination, metal examination, or the like), the selection unit 445 selects the inference result of the third inference unit 452 that performs inference on composite image data composed of material decomposition image data and CT image data (integral image data). Alternatively, the selection unit 445 may select the inference result of the first inference unit 450 that performs inference on material decomposition image data.

Composite image data composed of material decomposition image data and CT image data has a larger amount of information than material decomposition image data. Thus, the selection unit 445 selects the inference result of the third inference unit 452 that performs inference on composite image data composed of material decomposition image data and CT image data (integral image data), preferentially over the inference result of the first inference unit 450.

In a case where the examination order does not include the predetermined first examination, the selection unit 445 selects the inference result of the second inference unit 451 that performs inference on CT image data (integral image data). In a case where the examination order includes, for example, an examination regarding a node, the selection unit 445 selects the inference result of the second inference unit 451 that performs inference on CT image data (integral image data). In a case where the examination order includes an examination that is not executable only with material decomposition image data, the selection unit 445 selects the inference result of the second inference unit 451 that performs inference on CT image data (integral image data).

In a case where the examination order includes a predetermined second examination (an examination regarding breast cancer (a calcification examination and a tumor examination)), the inference result of the first inference unit 450 that performs inference on material decomposition image data including calcium information and the inference result of the second inference unit 451 that performs inference on CT image data (integral image data) are necessary. The second examination is different from the first examination. Thus, the selection unit 445 selects both the inference result of the first inference unit 450 that performs inference on material decomposition image data including calcium information and the inference result of the second inference unit 451 that performs inference on CT image data (integral image data).

The display control unit 446 controls the display unit 42 so as to display information on a progress status or a processing result in each function or processing of the processing circuit 44. The display control unit 446 causes the display unit 42 to display the inference result selected by the selection unit 445.

Figure 3:
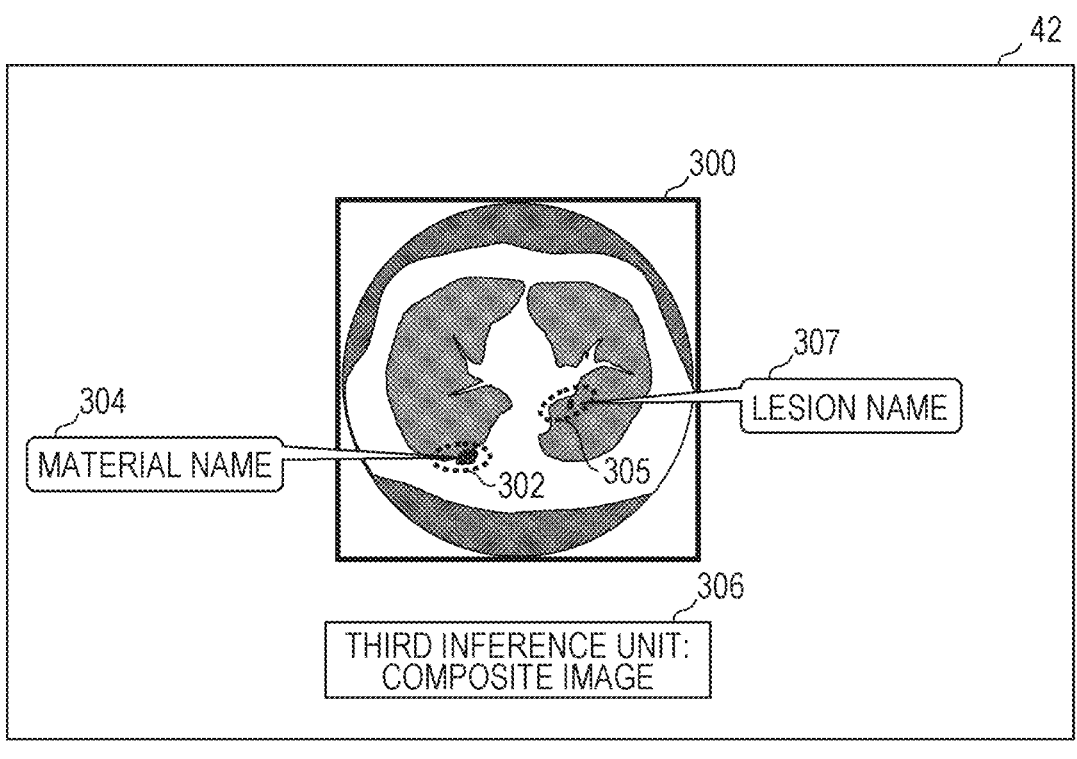
FIG. 3 is a diagram illustrating one display mode of a display unit in an X-ray CT apparatus according to an embodiment of the present disclosure.

FIG. 3 illustrates one display mode of the display unit 42 in the X-ray CT apparatus 1 according to an embodiment of the present disclosure. In response to the inference result of the third inference unit 452 that performs inference on composite image data composed of material decomposition image data and CT image data (integral image data) being selected by the selection unit 445, composite image data 300 composed of material decomposition image data and CT image data is displayed on the display unit 42 as illustrated in FIG. 3. The display unit 42 may display material decomposition image data.

The display unit 42 displays the composite image data 300 composed of material decomposition image data and CT image data (integral image data). The display unit 42 displays an image obtained by combining the respective sliced images of the material decomposition image data and the CT image data.

In response to a predetermined material (calcium, iodine, metal, or the like) being detected in the composite image data 300 composed of material decomposition image data and CT image data (integral image data) by the third inference unit 452, region information 302 and material name information 304 regarding the predetermined material are displayed. The operator is able to recognize which material is present at which position, from the region information 302 and the material name information 304 regarding the predetermined material. In response to a predetermined lesion being detected in the composite image data 300 composed of material decomposition image data and CT image data (integral image data) by the third inference unit 452, the display control unit 446 causes the display unit 42 to display region information 305 and lesion name information 307 regarding the lesion.

The display control unit 446 is also capable of causing the display unit 42 to display information 306 indicating that the third inference unit 452 has performed inference on the composite image data 300 composed of material decomposition image data and CT image data (integral image data). The operator is able to recognize that the composite image data 300 composed of material decomposition image data and CT image data (integral image data) has been used to infer the region information 302 and the material name information 304 regarding the predetermined material. Thus, the operator is able to recognize which material is present at which position. The operator is able to recognize that the composite image data 300 composed of material decomposition image data and CT image data (integral image data) has been used to infer the region information 305 and the lesion name information 307 regarding the lesion. Thus, the operator is able to recognize which lesion is present at which position.

In a case where the inference result of the first inference unit 450 that performs inference on material decomposition image data is different from the inference result of the second inference unit 451 that performs inference on CT image data (integral image data), the display control unit 446 is capable of causing the display unit 42 to display information indicating that the inference results are different from each other.

In a case where the inference result of the first inference unit 450 that performs a classification task is different from the inference result of the second inference unit 451 that performs a classification task, the display control unit 446 is capable of causing the display unit 42 to display classification information indicating that the inference results are different from each other. In a case where the inference result of the first inference unit 450 that performs a detection task is different from the inference result of the second inference unit 451 that performs a detection task, the display control unit 446 is capable of causing the display unit 42 to display detection information (region information) indicating that the inference results are different from each other.

Figure 4:
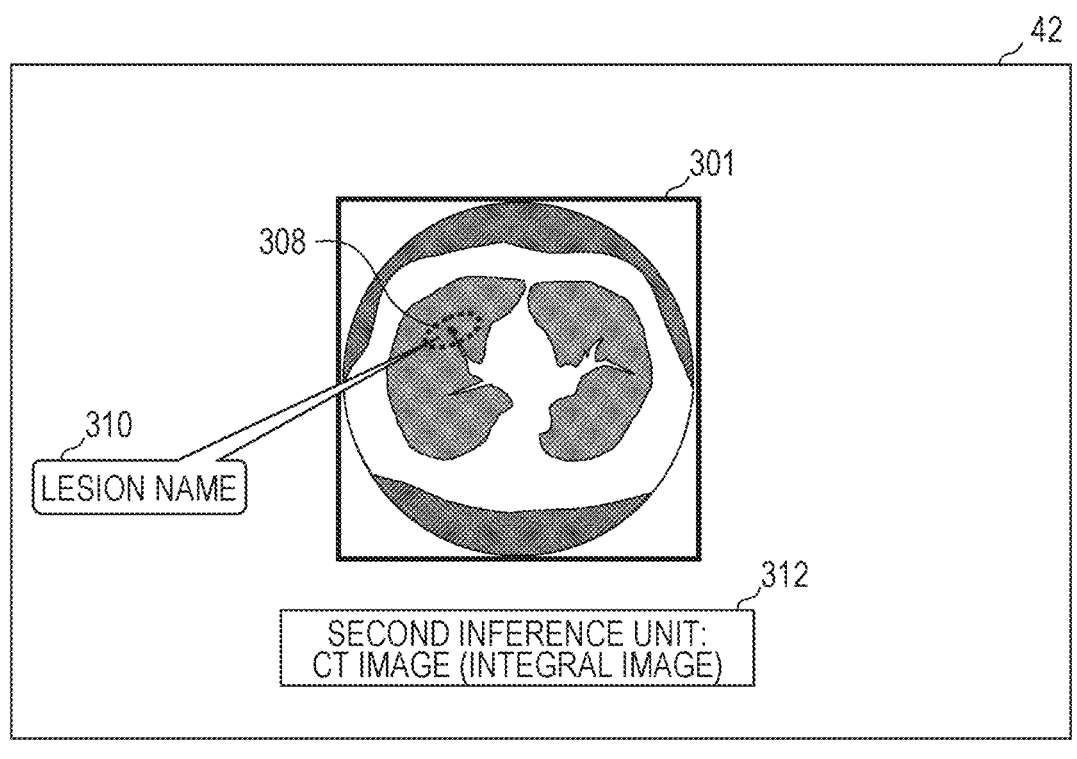
FIG. 4 is a diagram illustrating one display mode of a display unit in an X-ray CT apparatus according to an embodiment of the present disclosure.

FIG. 4 illustrates one display mode of the display unit 42 in the X-ray CT apparatus 1 according to an embodiment of the present disclosure. In response to the inference result of the second inference unit 451 that performs inference on CT image data (integral image data) being selected by the selection unit 445, CT image data 301 is displayed on the display unit 42 as illustrated in FIG. 4.

The display unit 42 displays the CT image data 301. The CT image data 301 is a sliced image of three-dimensional volume data. In response to a predetermined lesion (node, tumor, or the like) being detected in the CT image data 301 by the second inference unit 451, the display control unit 446 causes the display unit 42 to display region information 308 and lesion name information 310 regarding the predetermined lesion. The operator is able to recognize which lesion is present at which position, from the region information 308 and the lesion name information 310 regarding the predetermined lesion.

The display control unit 446 is also capable of causing the display unit 42 to display information 312 indicating that the second inference unit 451 has performed inference on the CT image data 301. The operator is able to recognize that the CT image data 301 has been used for inference.

Although the console device 40 has been described as a device that executes a plurality of functions by a single console, the plurality of functions may be executed by different consoles.

In a case where the inference result of the first inference unit 450 that performs inference on material decomposition image data is different from the inference result of the second inference unit 451 that performs inference on CT image data (integral image data), the display control unit 446 is capable of causing the display unit 42 to display information indicating that the inference results are different from each other. In a case where the inference result of the first inference unit 450 is different from the inference result of the second inference unit 451, the display control unit 446 is capable of causing the display unit 42 to display classification information or detection information (region information) indicating that the inference results are different from each other.

Figure 5:
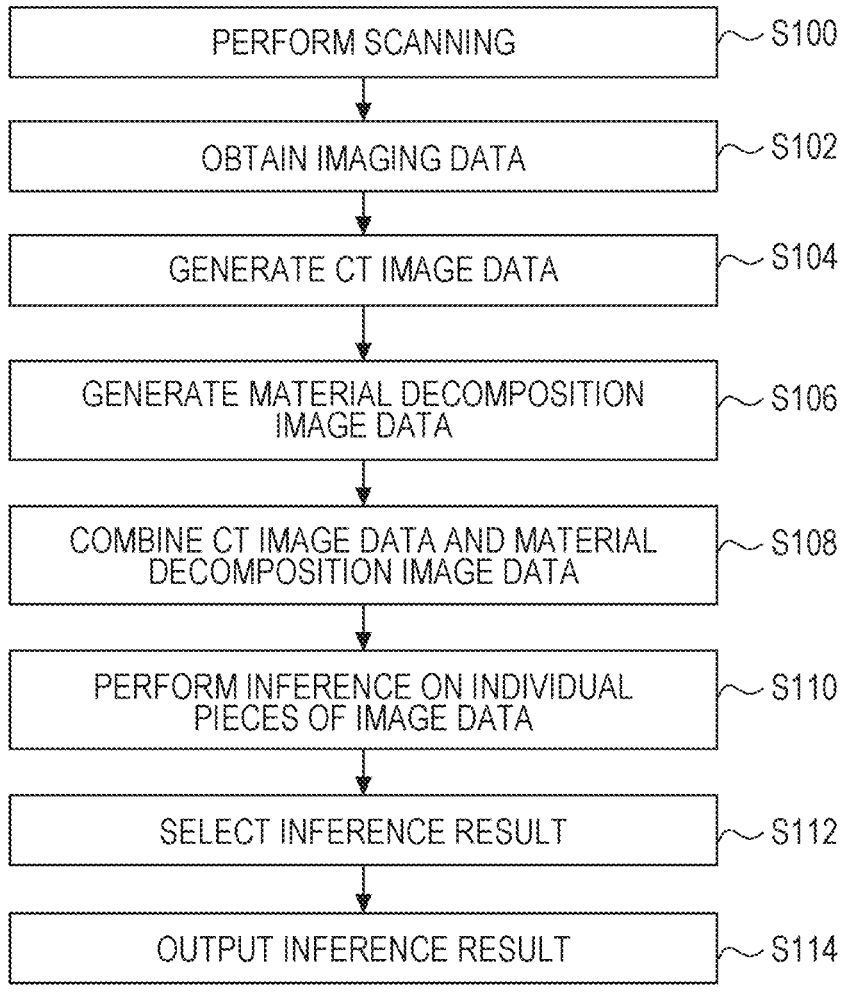
FIG. 5 is a flowchart illustrating an example operation of an X-ray CT apparatus according to an embodiment of the present disclosure.

Next, an operation of the X-ray CT apparatus 1 according to an embodiment of the present disclosure will be described. FIG. 5 is a flowchart illustrating an example operation of the X-ray CT apparatus 1.

S100: Scanning is performed to perform X-ray CT imaging on the subject P. X-ray CT imaging is performed, with X-rays being generated by the X-ray tube 11, and the X-ray tube 11 and the detector 12 being rotated about the rotational axis Z (the subject P).

S102: The detector 12 detects X-rays passed through the subject P, and obtains imaging data, which is a signal regarding the subject P. The imaging data is detection data obtained by bundling pieces of detection data from a predetermined number of detection elements in a spatial unit. The imaging data generated from a counting result obtained by the detector 12 includes information on the energy of X-rays attenuated as a result of passing through the subject P.

S104: The reconstruction processing unit 442 generates CT image data (integral image data), based on the imaging data output by the detector 12. The reconstruction processing unit 442 is capable of reconstructing, for example, image data of a specific energy component.

S106: The reconstruction processing unit 442 performs material decomposition on the imaging data output by the detector 12, and reconstructs material decomposition image data by using a result of the material decomposition. The reconstruction processing unit 442 generates material decomposition image data.

S108: The image combining unit 447 combines the material decomposition image data and the CT image data (integral image data). Specifically, the image combining unit 447 performs registration of the material decomposition image data and the CT image data, based on characteristic portions of the material decomposition image data and the CT image data, and combines the material decomposition image data and the CT image data.

S110: The first inference unit 450 performs inference on the material decomposition image data and obtains an inference result. The second inference unit 451 performs inference on the CT image data (integral image data) and obtains an inference result. The third inference unit 452 performs inference on the composite image data composed of the material decomposition image data and the CT image data (integral image data) and obtains an inference result.

S112: The selection unit 445 selects at least one of the inference result of the first inference unit 450 that performs inference on material decomposition image data, the inference result of the second inference unit 451 that performs inference on CT image data (integral image data), and the inference result of the third inference unit 452 that performs inference on composite image data composed of material decomposition image data and CT image data (integral image data).

S114: The selection unit 445 outputs the selected inference result to the display control unit 446. The display control unit 446 causes the display unit 42 to display the inference result of the third inference unit 452 and the composite image data 300 composed of the material decomposition image data and the CT image data (integral image data), as illustrated in FIG. 3.

In a case where the inference result of the third inference unit 452 includes a predetermined material (calcium, iodine, metal, or the like), the display control unit 446 causes the display unit 42 to display the region information 302 and the material name information 304 regarding the predetermined material. In a case where the inference result of the third inference unit 452 includes a lesion, the display control unit 446 causes the display unit 42 to display the region information 305 and the lesion name information 307 regarding the lesion.

The selection unit 445 may select both the inference result of the first inference unit 450 that performs inference on material decomposition image data and the inference result of the second inference unit 451 that performs inference on CT image data (integral image data). In this case, the selection unit 445 outputs the inference result of the first inference unit 450 and the inference result of the second inference unit 451 to the display control unit 446. The display control unit 446 is capable of causing the display unit 42 to display, on the same screen, composite image data composed of the material decomposition image data and the CT image data, the inference result of the first inference unit 450, and the inference result of the second inference unit 451.

The inference result of the second inference unit 451 may be output to the display control unit 446. The display control unit 446 causes the display unit 42 to display the inference result of the second inference unit 451 and the CT image data 301, as illustrated in FIG. 4. The display control unit 446 is capable of causing the display unit 42 to display, on the same screen, the CT image data 301 and the inference result of the second inference unit 451. In a case where the inference result of the second inference unit 451 includes a lesion, the display control unit 446 causes the display unit 42 to display the region information 308 and the lesion name information 310 regarding the lesion.

As described above, the inference unit 444 includes the first inference unit 450 that performs inference on material decomposition image data by using a neural network, the second inference unit 451 that performs inference on CT image data by using a neural network, and the third inference unit 452 that performs inference on composite image data composed of material decomposition image data and CT image data (integral image data).

In a case where an inference result obtained by performing inference on composite image data composed of material decomposition image data and CT image data (integral image data) or on material decomposition image data includes information regarding a specific material, the selection unit 445 selects the inference result obtained by performing inference on the composite image data composed of material decomposition image data and CT image data (integral image data) or on the material decomposition image data. In a case where an inference result obtained by performing inference on CT image data (integral image data) includes information regarding a specific lesion, the selection unit 445 selects the inference result obtained by performing inference on the CT image data (integral image data).

In a case where an inference result obtained by performing inference on material decomposition image data includes information regarding a specific material and where an inference result obtained by performing inference on CT image data (integral image data) includes information regarding a specific lesion, the selection unit 445 selects the inference result obtained by performing inference on the material decomposition image data and the inference result obtained by performing inference on the CT image data (integral image data).

As illustrated in FIG. 5, in S110, the first inference unit 450 performs inference on the material decomposition image data and obtains an inference result. The second inference unit 451 performs inference on the CT image data (integral image data) and obtains an inference result. The third inference unit 452 performs inference on the composite image data composed of the material decomposition image data and the CT image data (integral image data) and obtains an inference result.

The control unit 441 is capable of comparing the inference result of the first inference unit 450 obtained by performing inference on the material decomposition image data, the inference result of the second inference unit 451 obtained by performing inference on the CT image data (integral image data), and the inference result of the third inference unit 452 obtained by performing inference on the composite image data composed of the material decomposition image data and the CT image data (integral image data) with each other, calculating comparison information of the inference results, and causing the comparison information to be displayed. The comparison information of the inference results indicates whether the inference result of the first inference unit 450 obtained by performing inference on the material decomposition image data, the inference result of the second inference unit 451 obtained by performing inference on the CT image data (integral image data), and the inference result of the third inference unit 452 obtained by performing inference on the composite image data composed of the material decomposition image data and the CT image data (integral image data) match with each other.

For example, in a case where the inference result of the first inference unit 450 obtained by performing inference on the material decomposition image data matches the inference result of the second inference unit 451 obtained by performing inference on the CT image data (integral image data), the selection unit 445 selects either one of the inference result of the first inference unit 450 obtained by performing inference on the material decomposition image data and the inference result of the second inference unit 451 obtained by performing inference on the CT image data (integral image data). The display control unit 446 may cause the display unit 42 to display information indicating that the inference result of the first inference unit 450 obtained by performing inference on the material decomposition image data matches the inference result of the second inference unit 451 obtained by performing inference on the CT image data (integral image data).

In a case where the inference result of the first inference unit 450 obtained by performing inference on the material decomposition image data is different from the inference result of the second inference unit 451 obtained by performing inference on the CT image data (integral image data), there is a possibility that material decomposition affects the inference results, and thus the selection unit 445 selects the inference result of the third inference unit 452 obtained by performing inference on the composite image data composed of the material decomposition image data and the CT image data (integral image data). The display control unit 446 causes the display unit 42 to display the inference result of the third inference unit 452 obtained by performing inference on the composite image data composed of the material decomposition image data and the CT image data (integral image data), and the composite image data 300, as illustrated in FIG. 3.

In a case where the inference result of the first inference unit 450 obtained by performing inference on the material decomposition image data is different from the inference result of the second inference unit 451 obtained by performing inference on the CT image data (integral image data), the selection unit 445 may select the inference result of the first inference unit 450 obtained by performing inference on the material decomposition image data, and the inference result of the second inference unit 451 obtained by performing inference on the CT image data (integral image data). The display control unit 446 may cause the display unit 42 to display information indicating that the inference result of the first inference unit 450 obtained by performing inference on the material decomposition image data is different from the inference result of the second inference unit 451 obtained by performing inference on the CT image data (integral image data).

The display control unit 446 may perform emphasized display for a region in which the inference result of the first inference unit 450 obtained by performing inference on the material decomposition image data is different from the inference result of the second inference unit 451 obtained by performing inference on the CT image data (integral image data). The emphasized display is frame display, highlight display, or the like. The display control unit 446 is capable of performing display such that a region in which the inference result of the first inference unit 450 obtained by performing inference on the material decomposition image data is different from the inference result of the second inference unit 451 obtained by performing inference on the CT image data (integral image data) can be distinguished.

The display control unit 446 may cause the display unit 42 to display, on composite image data composed of the material decomposition image data and the CT image data (integral image data), the inference result of the first inference unit 450 obtained by performing inference on the material decomposition image data and the inference result of the second inference unit 451 obtained by performing inference on the CT image data (integral image data). The operator is able to recognize, from the individual inference results (detection information), which detection information has a difference.

As described above, the X-ray CT apparatus according to the present embodiment includes the X-ray tube 11 configured to radiate X-rays; the detector 12 configured to detect X-rays radiated by the X-ray tube 11 and passed through a subject; the reconstruction processing unit 442 configured to reconstruct imaging data output by the detector 12 and generate CT image data and material decomposition image data; the first inference unit 450 configured to perform inference on the material decomposition image data; the second inference unit 451 configured to perform inference on the CT image data; the third inference unit 452 configured to perform inference on composite image data composed of the CT image data and the material decomposition image data; the selection unit 445 configured to, in a case where an inference result of the first inference unit 450 is different from an inference result of the second inference unit 451, select an inference result of the third inference unit 452; and the display control unit 446 configured to cause the selected inference result of the third inference unit 452 to be displayed. In a case where the inference result of the first inference unit 450 is the same as the inference result of the second inference unit 451, the display control unit 446 causes either one of the inference result of the first inference unit 450 and the inference result of the second inference unit 451 to be displayed.

Accordingly, the X-ray CT apparatus according to the present embodiment is capable of displaying an appropriate inference result in accordance with a situation of a plurality of inference results.

The detector need not necessarily be the detector of the X-ray CT apparatus. A detector of an X-ray imaging apparatus may be used.

The information processing system according to the present embodiment includes the first inference unit 450 configured to perform inference on material decomposition image data generated by reconstructing imaging data output by a detector; the second inference unit 451 configured to perform inference on image data generated by reconstructing the imaging data output by the detector; the third inference unit 452 configured to perform inference on composite image data composed of the image data and the material decomposition image data; the selection unit 445 configured to, in a case where an inference result of the first inference unit 450 is different from an inference result of the second inference unit 451, select an inference result of the third inference unit 452; and the display control unit 446 configured to cause the selected inference result of the third inference unit 452 to be displayed.

The information processing method according to the present embodiment includes performing inference on material decomposition image data generated by reconstructing imaging data output by a detector; performing inference on image data generated by reconstructing the imaging data output by the detector; selecting an inference result obtained by performing inference on composite image data composed of the image data and the material decomposition image data, in a case where an inference result obtained in the performing of the inference on the material decomposition image data is different from an inference result obtained in the performing of the inference on the image data; and causing the selected inference result to be displayed.

Next, a second embodiment of the present disclosure will be described. The second embodiment is different from the first embodiment in that the selection unit 445 selects at least one of the first inference unit 450 that performs inference on material decomposition image data, the second inference unit 451 that performs inference on CT image data (integral image data), and the third inference unit 452 that performs inference on composite image data composed of CT image data and material decomposition image data. In the present embodiment, differences from the first embodiment will be mainly described.

In the case of selecting material decomposition image data as an inference target, the selection unit 445 selects the first inference unit 450 or the third inference unit 452. The first inference unit 450 performs inference on material decomposition image data. The third inference unit 452 performs inference on composite image data composed of CT image data and material decomposition image data. In the case of not selecting material decomposition image data as an inference target, the selection unit 445 selects the second inference unit 451. The second inference unit 451 performs inference on CT image data (integral image data).

The reconstruction processing unit 442 has a function of generating CT image data (integral image data), based on imaging data output by the detector 12. The display control unit 446 causes the display unit 42 to display the CT image data. The reconstruction processing unit 442 also has a function of performing material decomposition on imaging data output by the detector 12 and reconstructing material decomposition image data by using a result of the material decomposition. The display control unit 446 is capable of causing the display unit 42 to display the material decomposition image data.

The selection unit 445 determines whether to select material decomposition image data as an inference target. In the case of selecting material decomposition image data as an inference target, the third inference unit 452 performs inference on composite image data composed of CT image data and material decomposition image data, and obtains an inference result. The first inference unit 450 may perform inference on material decomposition image data and obtain an inference result. The third inference unit 452 or the first inference unit 450 outputs the inference result of the third inference unit 452 or the inference result of the first inference unit 450 to the display control unit 446.

Next, a third embodiment of the present disclosure will be described with reference to FIGS. 6 and 7. The third embodiment is different from the first and second embodiments in that the image analysis unit 443 that analyzes material decomposition image data and obtains content information of a predetermined material or a predetermined lesion included in the material decomposition image data is provided, and that the selection unit 445 selects, based on the content information of the predetermined material or the predetermined lesion included in the material decomposition image data, an inference result of the third inference unit 452 that performs inference on composite image data composed of CT image data and material decomposition image data. In the present embodiment, differences from the first and second embodiments will be mainly described.

Figure 6:
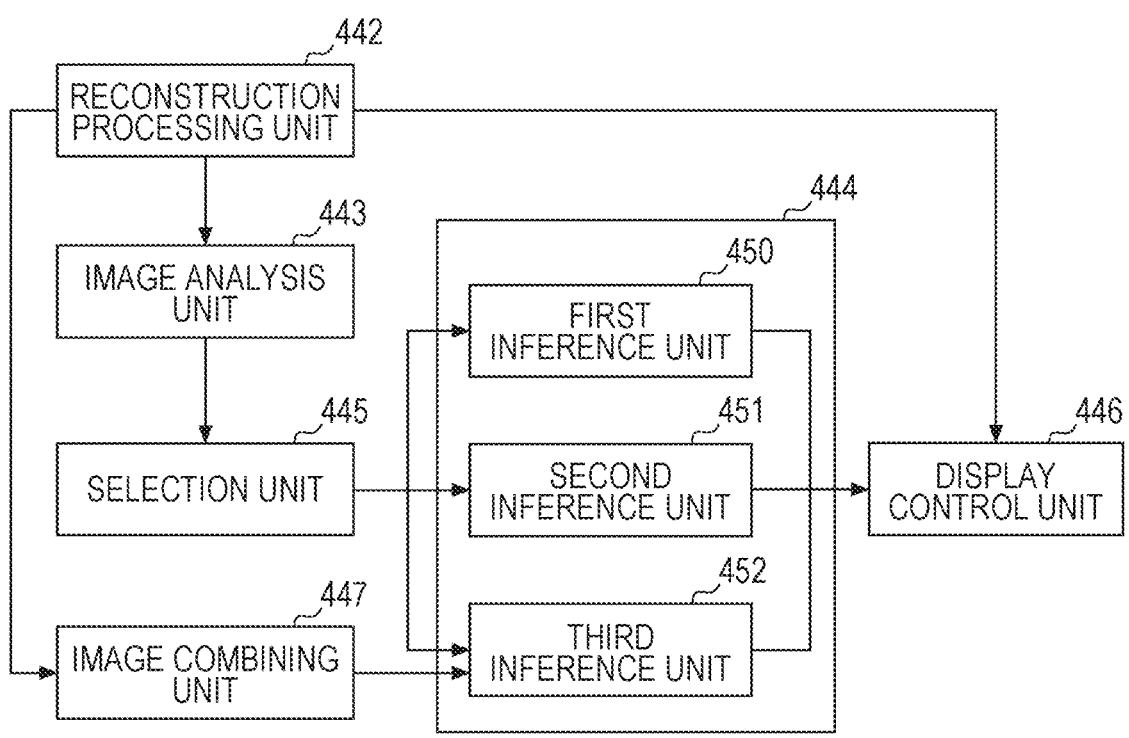
FIG. 6 is a diagram illustrating an example of a peripheral configuration of an inference unit of an X-ray CT apparatus according to an embodiment of the present disclosure.
Figure 7:
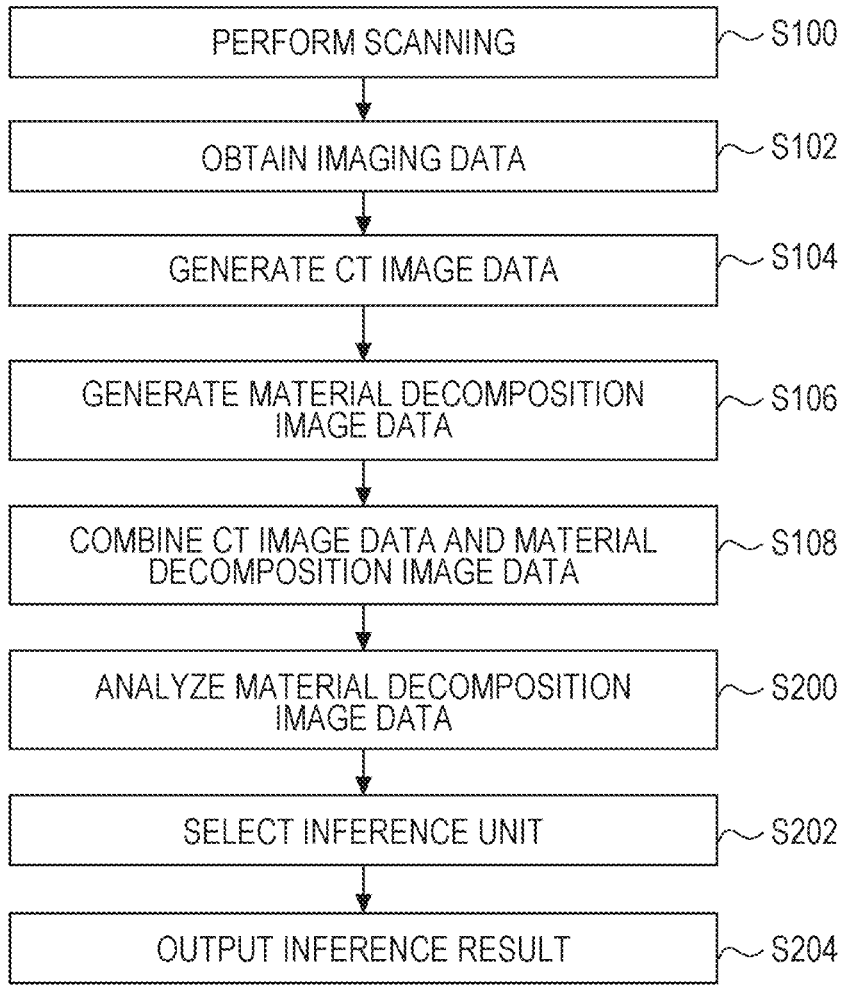
FIG. 7 is a flowchart illustrating an example operation of an X-ray CT apparatus according to an embodiment of the present disclosure.

As illustrated in FIG. 6, the reconstruction processing unit 442 has a function of generating CT image data (integral image data), based on imaging data output by the detector 12. The display control unit 446 causes the display unit 42 to display the CT image data. The reconstruction processing unit 442 performs material decomposition on the imaging data output by the detector 12, and reconstructs material decomposition image data by using a result of the material decomposition. The display control unit 446 is capable of causing the display unit 42 to display the material decomposition image data.

The image analysis unit 443 analyzes material decomposition image data. The image analysis unit 443 is capable of analyzing material decomposition image data and obtaining the type and amount of material included in the material decomposition image data. That is, the image analysis unit 443 obtains content information of a predetermined material included in the material decomposition image data. The selection unit 445 is capable of selecting an inference target, based on an analysis result of the image analysis unit 443, that is, based on content information of a predetermined material included in the material decomposition image data. In other words, the selection unit 445 selects, based on an analysis result of the image analysis unit 443, that is, based on content information of a predetermined material included in the material decomposition image data, at least one of the first inference unit 450 that performs inference on material decomposition image data, the second inference unit 451 that performs inference on CT image data (integral image data), and the third inference unit 452 that performs inference on composite image data composed of CT image data and material decomposition image data.

The predetermined material is any one of calcium, water, iodine, and the like. The image analysis unit 443 is capable of obtaining, as content information of the predetermined material in the material decomposition image data, for example, the percentage of calcium included in the material decomposition image data. The image analysis unit 443 is also capable of determining whether calcium is included in the material decomposition image data at a predetermined ratio or more (at a predetermined content or more). In a case where calcium is included in the material decomposition image data at a predetermined ratio or more (at a predetermined content or more), the selection unit 445 selects the third inference unit 452 that performs inference on composite image data composed of CT image data and material decomposition image data. The selection unit 445 may select the first inference unit 450 that performs inference on material decomposition image data.

In a case where calcium is not included in the material decomposition image data at a predetermined ratio or more (at a predetermined content or more), the selection unit 445 selects the second inference unit 451 that performs inference on CT image data (integral image data).

The image analysis unit 443 is capable of obtaining, as content information of the predetermined material in the material decomposition image data, for example, the percentage of water included in the material decomposition image data. Water corresponds to, for example, blood, lymph, or the like. The image analysis unit 443 is also capable of determining whether water is included in the material decomposition image data at a predetermined ratio or more (at a predetermined content or more). In a case where water is included in the material decomposition image data at a predetermined ratio or more (at a predetermined content or more), the selection unit 445 selects the third inference unit 452 that performs inference on composite image data composed of CT image data and material decomposition image data. The selection unit 445 may select the first inference unit 450 that performs inference on material decomposition image data. In a case where water is not included in the material decomposition image data at a predetermined ratio or more (at a predetermined content or more), the selection unit 445 selects the second inference unit 451 that performs inference on CT image data (integral image data).

The image analysis unit 443 is capable of obtaining, as content information of the predetermined material in the material decomposition image data, for example, the percentage of iodine included in the material decomposition image data. The image analysis unit 443 is also capable of determining whether iodine is included in the material decomposition image data at a predetermined ratio or more (at a predetermined content or more). In a case where iodine is included in the material decomposition image data at a predetermined ratio or more (at a predetermined content or more), the selection unit 445 selects the third inference unit 452 that performs inference on composite image data composed of CT image data and material decomposition image data. The selection unit 445 may select the first inference unit 450 that performs inference on material decomposition image data. In a case where iodine is not included in the material decomposition image data at a predetermined ratio or more (at a predetermined content or more), the selection unit 445 selects the second inference unit 451 that performs inference on CT image data (integral image data).

That is, in a case where a predetermined material is included in the material decomposition image data at a predetermined ratio or more, the selection unit 445 selects the third inference unit 452. The third inference unit 452 is selected preferentially over the first inference unit 450. In a case where a predetermined material is not included in the material decomposition image data at a predetermined ratio or more, the selection unit 445 selects the second inference unit 451.

A setting unit (operation unit 43) for setting the type of material to be analyzed by the image analysis unit 443 may be provided. The operator is able to select, via the setting unit, the type of material to be analyzed by the image analysis unit 443. As a material to be analyzed by the image analysis unit 443, the operator selects, for example, calcium via the setting unit. In a case where calcium is included in the material decomposition image data at a predetermined ratio or more (at a predetermined content or more), the selection unit 445 selects the third inference unit 452 that performs inference on composite image data composed of CT image data and material decomposition image data. In a case where calcium is not included in the material decomposition image data at a predetermined ratio or more (at a predetermined content or more), the selection unit 445 selects the second inference unit 451 that performs inference on CT image data (integral image data).

As a material to be analyzed by the image analysis unit 443, the operator selects, for example, iodine via the setting unit. In a case where iodine is included in the material decomposition image data at a predetermined ratio or more (at a predetermined content or more), the selection unit 445 selects the third inference unit 452 that performs inference on composite image data composed of CT image data and material decomposition image data. In a case where iodine is not included in the material decomposition image data at a predetermined ratio or more (at a predetermined content or more), the selection unit 445 selects the second inference unit 451 that performs inference on CT image data (integral image data).

As a material and lesion to be analyzed by the image analysis unit 443, the operator is able to select, for example, calcium and tumor via the setting unit. In a case where the material (calcium) is included in the material decomposition image data at a predetermined ratio or more (at a predetermined content or more) or in a case where the lesion (tumor) is included in the material decomposition image data at a predetermined ratio or more (at a predetermined content or more), the selection unit 445 selects the third inference unit 452 that performs inference on composite image data composed of CT image data and material decomposition image data.

Next, an operation of the X-ray CT apparatus 1 according to an embodiment of the present disclosure will be described. FIG. 7 is a flowchart illustrating an example operation of the X-ray CT apparatus 1.

S100 to S108 are the same as in FIG. 5, and thus the description thereof will be omitted.

S200: The image analysis unit 443 analyzes material decomposition image data. The image analysis unit 443 analyzes material decomposition image data and is capable of obtaining the type and amount of material included in the material decomposition image data, or the type and amount of lesion included in the material decomposition image data. That is, the image analysis unit 443 obtains content information of a predetermined material included in the material decomposition image data or content information of a predetermined lesion included in the material decomposition image data.

S202: The selection unit 445 selects an inference target, based on an analysis result of the image analysis unit 443, that is, content information of a predetermined material included in the material decomposition image data or content information of a predetermined lesion included in the material decomposition image data. The selection unit 445 selects at least one of the first inference unit 450 that performs inference on material decomposition image data, the second inference unit 451 that performs inference on CT image data (integral image data), and the third inference unit 452 that performs inference on composite image data composed of CT image data and material decomposition image data.

S204: The selected inference unit outputs the inference result of the inference unit to the display control unit 446. The display control unit 446 causes the display unit 42 to display the inference result of the selected inference unit and the composite image data 300. The display control unit 446 may cause the display unit 42 to display the analysis result of the image analysis unit 443. Specifically, the display control unit 446 is capable of causing the display unit 42 to display content information of a predetermined material included in the material decomposition image data or content information of a predetermined lesion included in the material decomposition image data.

As described above, the X-ray CT apparatus according to the present embodiment includes the X-ray tube 11 configured to radiate X-rays; the detector 12 configured to detect X-rays radiated by the X-ray tube 11 and passed through a subject; the reconstruction processing unit 442 configured to reconstruct imaging data output by the detector 12 and generate CT image data and material decomposition image data; the first inference unit 450 configured to perform inference on the material decomposition image data; the second inference unit 451 configured to perform inference on the CT image data; the third inference unit 452 configured to perform inference on composite image data composed of the CT image data and the material decomposition image data; the image analysis unit 443 configured to analyze the material decomposition image data and obtain content information of a predetermined material included in the material decomposition image data or content information of a predetermined lesion included in the material decomposition image data; the selection unit 445 configured to, based on the content information of the predetermined material included in the material decomposition image data or the content information of the predetermined lesion included in the material decomposition image data, select the third inference unit 452; and the display control unit 446 configured to cause an inference result of the selected third inference unit 452 to be displayed. Accordingly, the operator is able to confirm an inference result corresponding to the material decomposition image data.

The detector need not necessarily be the detector of the X-ray CT apparatus. A detector of an X-ray imaging apparatus may be used.

The information processing system according to the present embodiment includes the first inference unit 450 configured to perform inference on material decomposition image data generated by reconstructing imaging data output by a detector; the second inference unit 451 configured to perform inference on image data generated by reconstructing the imaging data output by the detector; the third inference unit 452 configured to perform inference on composite image data composed of the image data and the material decomposition image data; the image analysis unit 443 configured to analyze the material decomposition image data and obtain content information of a predetermined material included in the material decomposition image data or content information of a predetermined lesion included in the material decomposition image data; the selection unit 445 configured to, based on the content information of the predetermined material included in the material decomposition image data or the content information of the predetermined lesion included in the material decomposition image data, select the third inference unit 452; and the display control unit 446 configured to cause an inference result of the selected third inference unit 452 to be displayed.

The information processing method according to the present embodiment includes analyzing material decomposition image data generated by reconstructing imaging data output by a detector and obtaining content information of a predetermined material included in the material decomposition image data or content information of a predetermined lesion included in the material decomposition image data; and performing, based on the content information of the predetermined material included in the material decomposition image data or the content information of the predetermined lesion included in the material decomposition image data, inference on composite image data composed of image data and the material decomposition image data, and causing an inference result to be displayed.

A computer program that implements the functions of the above-described embodiments may be supplied to a computer via a network or a memory (storage medium), and the computer program may be executed by a processor (not illustrated). The computer program causes the computer to execute the above-described information processing method. That is, the computer program is a program for implementing the functions of the information processing system by the computer. The memory stores the computer program.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2022-177876, filed Nov. 7, 2022, which is hereby incorporated by reference herein in its entirety.

What is claimed is:

1. An X-ray computed tomography (CT) apparatus comprising:

an X-ray tube configured to radiate X-rays;

an X-ray detector configured to detect X-rays radiated by the X-ray tube and passed through a subject, and at least one processor configured to execute instructions to reconstruct imaging data output by the X-ray detector and generate CT image data and material decomposition image data;

perform a first inference on the material decomposition image data;

perform a second inference on the CT image data;

perform a third inference on composite image data composed of the CT image data and the material decomposition image data;

select, in a case where an inference result of the first inference is different from an inference result of the second inference, an inference result of the third inference; and cause the selected inference result of the third inference to be displayed.

2. The X-ray CT apparatus according to claim 1, wherein the at least one processor is configured to, in a case where the inference result of the first inference is the same as the inference result of the second inference, cause either one of the inference result of the first inference and the inference result of the second inference to be displayed.

3. The X-ray CT apparatus according to claim 1, wherein the CT image data is integral image data.

4. The X-ray CT apparatus according to claim 1, wherein the at least one processor is configured to, in response to a predetermined material being detected in the material decomposition image data in the first inference, cause region information and material name information regarding the predetermined material to be displayed.

5. The X-ray CT apparatus according to claim 1, wherein the at least one processor is configured to cause information to be displayed, the information indicating that inference has been performed on the composite image data composed of the CT image data and the material decomposition image data.

6. The X-ray CT apparatus according to claim 1, wherein the at least one processor is configured to, in response to a predetermined lesion being detected in the CT image data in the second inference, cause region information and lesion name information regarding the predetermined lesion to be displayed.

7. The X-ray CT apparatus according to claim 1, wherein the at least one processor is configured to cause information to be displayed, the information indicating that inference has been performed on the CT image data.

8. An X-ray computed tomography (CT) apparatus comprising:

an X-ray tube configured to radiate X-rays;

a detector configured to detect X-rays radiated by the X-ray tube and passed through a subject, and at least one processor configured to execute instructions to reconstruct imaging data output by the detector and generate CT image data and material decomposition image data;

perform a first inference on the material decomposition image data;

perform a second inference on the CT image data;

perform a third inference on composite image data composed of the CT image data and the material decomposition image data;

analyze the material decomposition image data and obtain content information of a predetermined material included in the material decomposition image data or content information of a predetermined lesion included in the material decomposition image data;

select, based on the content information of the predetermined material included in the material decomposition image data or the content information of the predetermined lesion included in the material decomposition image data, at least one of an inference result of the first inference, an inference result of the second inference, and an inference result of the third inference; and cause the selected inference result to be displayed.

9. The X-ray CT apparatus according to claim 8, wherein the predetermined material is any one of calcium, water, and iodine.

10. The X-ray CT apparatus according to claim 8, wherein the at least one processor is configured to, in a case where the predetermined material is included in the material decomposition image data at a predetermined ratio or more, select the inference result of the third inference.

11. The X-ray CT apparatus according to claim 8, wherein the at least one processor is configured to, in a case where the predetermined material is not included in the material decomposition image data at a predetermined ratio or more, select the inference result of the second inference.

12. The X-ray CT apparatus according to claim 8, the at least one processor is further configured to set a type of a material to be analyzed.

13. An X-ray computed tomography (CT) apparatus comprising:

an X-ray tube configured to radiate X-rays;

a detector configured to detect X-rays radiated by the X-ray tube and passed through a subject;

at least one processor configured to execute instructions to reconstruct imaging data output by the detector and generate CT image data and material decomposition image data;

perform a first inference on the material decomposition image data;

perform a second inference on the CT image data;

perform a third inference on composite image data composed of the CT image data and the material decomposition image data; and select at least one of an inference result of the first inference, an inference result of the second inference, and an inference result of the third inference in accordance with an examination order.

14. An information processing system comprising:

at least one processor configured to execute instructions to perform a first inference on material decomposition image data generated by reconstructing imaging data output by a detector;

perform a second inference on image data generated by reconstructing the imaging data output by the detector;

perform a third inference on composite image data composed of the image data and the material decomposition image data;

select, in a case where an inference result of the first inference is different from an inference result of the second inference, an inference result of the third inference; and cause the selected inference result of the third inference to be displayed.

* * * * *